United States Patent [19]

Kronwald

[11] Patent Number: 5,188,730
[45] Date of Patent: Feb. 23, 1993

[54] MULTIPART CHROMATOGRAPHY COLUMN CONNECTION

[75] Inventor: Klaus Kronwald, Sinsheim, Fed. Rep. of Germany

[73] Assignee: Kronwald Separationstechnik GmbH, Sinsheim, Fed. Rep. of Germany

[21] Appl. No.: 695,811

[22] Filed: May 7, 1991

[30] Foreign Application Priority Data

May 7, 1990 [DE] Fed. Rep. of Germany ....... 4014605

[51] Int. Cl.⁵ .............................................. B01D 15/08
[52] U.S. Cl. .................................. 210/198.2; 210/94; 55/386
[58] Field of Search ................ 210/94, 95, 198.2, 450, 210/656, 659; 55/386

[56] References Cited

U.S. PATENT DOCUMENTS

| | | | |
|---|---|---|---|
| 3,474,908 | 10/1969 | Catravas | 210/198.2 |
| 3,483,986 | 12/1969 | Wright | 210/198.2 |
| 3,487,938 | 1/1970 | Patterson | 210/198.2 |
| 3,511,377 | 5/1970 | Hrdina | 55/386 |
| 3,791,522 | 2/1974 | Eisenbeiss | 210/198.2 |
| 3,878,099 | 4/1975 | Ogle | 210/198.2 |
| 4,168,235 | 9/1979 | Guillemin | 210/198.2 |
| 4,350,595 | 9/1982 | Gunkel | 210/198.2 |
| 4,361,482 | 11/1982 | Teetz | 210/198.2 |
| 4,451,365 | 5/1984 | Sattler | 210/198.2 |
| 4,476,017 | 10/1984 | Scharff | 210/198.2 |
| 4,636,315 | 1/1987 | Allen | 210/198.2 |
| 4,769,141 | 9/1988 | Couillard | 210/198.2 |
| 4,787,284 | 4/1988 | Hauke | 210/198.2 |
| 4,792,396 | 12/1988 | Gundelfinger | 210/198.2 |
| 4,865,728 | 9/1989 | Larsson | 210/198.2 |
| 4,888,112 | 12/1989 | Kronwald | 210/198.2 |
| 4,927,531 | 5/1990 | Sakamoto | 210/198.2 |

FOREIGN PATENT DOCUMENTS

| | | | |
|---|---|---|---|
| 509591 | 8/1970 | Switzerland | 210/198.2 |
| 868586 | 9/1981 | U.S.S.R. | 210/198.2 |

Primary Examiner—Ernest G. Therkorn
Attorney, Agent, or Firm—Foley & Lardner

[57] ABSTRACT

A multipart chromatography column connection having a two-part screwed union anchored on the head of a column body or on the thread of a metal column or a surrounding jacket is disclosed. The connection has an upper part and a lower part, a bushing, fixed therein, with a capillary and a sealing insert of soft plastic at the end. The upper part of the screwed union has a window in which a nut is arranged for free turning. The bushing has an external thread which meshes with the nut. The nut and bushing are made of a hard material. An adaptor, also made of hard material, is screwed to the lower end of the bushing, the capillary being held in sealing compression between the adaptor and the bushing. The sealing insert is screwed to the free end of the adaptor and the adaptor and sealing insert have mutually aligned bores, which are connected to the capillary, and which have sealing surfaces bearing against one another. A method for filling a chromatography column is also disclosed, in which the column is filled with a suspension of packing material and the carrier fluid is expelled under pressure by a ram.

10 Claims, 5 Drawing Sheets

MULTIPART CHROMATOGRAPHY COLUMN CONNECTION

BACKGROUND OF THE INVENTION

The present invention relates to a multipart connection for chromatography columns for carrying out separations of substances on variable packing materials which are packed in a column body. The column body can be made of glass, ceramic, sapphire or stainless steel. The packing materials can be silica gel, silica gel derivatives or solid polymer gels of different type or agarose gels or polyacrylamide gels. There are three versions of the column body, namely cylindrical with connecting flanges at the end, cylindrical with external threads at the end and cylindrical without flanges and without external threads at the end.

In chromatography columns, a carrier fluid transports dissolved sample substances through a capillary tube running around a connection into a column interior. At the end of the column connection, the fluid is passed through a frit of fine-pored sintered glass, ceramic or stainless steel, in order to ensure uniform distribution over the column cross-section.

The filling of the column with very fine pulverulent packing materials can be effected with the aid of a suspension of this material, the suspension being filled into the column and then being compressed by a piston. Carrier fluid thus emerges. As a result of this compaction of the packing particles, an optimum spatial arrangement of the particles is achieved, so that a uniform column bed is produced.

For this packing step, the chromatography column must normally be clamped into a device, in which a piston, after the column has been introduced, is forced upon the suspension under a mechanical load. After the compaction, this piston must be carefully removed and the actual chromatography column connection must be introduced.

This procedure is very involved since it requires additional mechanical devices. Moreover, the homogeneity of the column packing is disturbed by the change in load when the piston is withdrawn, so that the performance capacity of the column is impaired.

SUMMARY OF THE INVENTION

It is therefore an object of the present invention to provide a column connection for the above-mentioned purpose, by means of which direct expulsion of the carrier fluid is possible, without impairment of the quality of the column, especially at the frequently required high pressures of up to more than 120 bar.

It is a further object of the invention to provide a chromatography column connection which ensures that further settling of the column packing during later operation of the column, such as can occur naturally, can easily be compensated without the column having to be opened. This eliminates removal of the column connection, so that the column packing cannot be destroyed.

These and other objects according to the invention are provided by a multipart chromatography column connection having a two-part screwed union anchored on a bead of a column body or on a thread of a metal column or its surrounding jacket, comprising an upper part having a window in which a nut is arranged for free turning; a bushing having an external thread which meshes with the nut; an adaptor screwed to a lower end of the bushing; a capillary held in sealing compression between the adaptor and the bushing; and a sealing insert screwed to the free end of the adaptor, wherein the adaptor and sealing insert have mutually-aligned bores which are connected to the capillary and which have sealing surfaces bearing against one another.

The present invention also provides a method for separating materials with a chromatography column, comprising the steps of filling a chromatography column with a suspension of packing material; placing a sealing insert on top of the suspension; moving the sealing insert against the suspension by means of a bushing which acts as a spindle to expel carrier fluid; leaving the sealing insert and the bushing in place in the column; and carrying out a chromatographic separation with the packed column.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
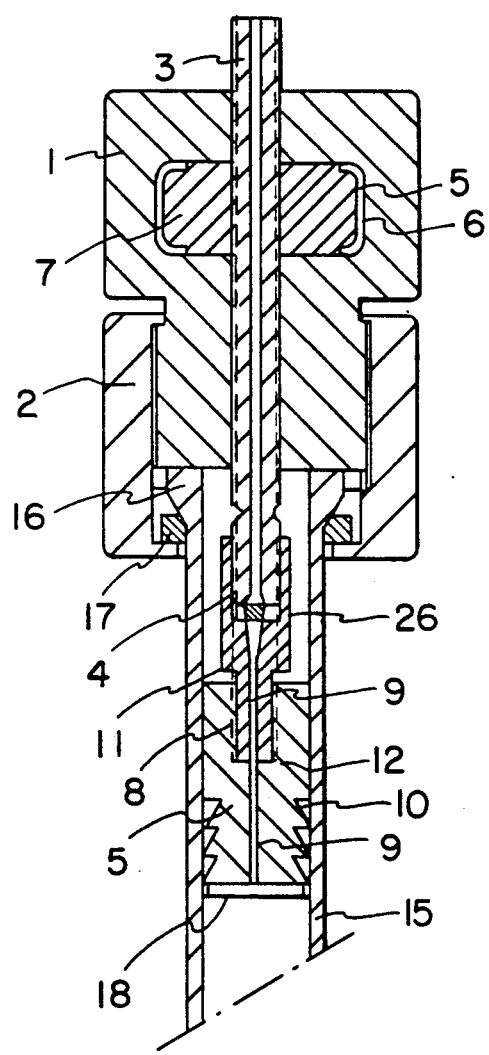
FIG. 1 shows a first embodiment of a chromatography column connection according to the invention, in which the column body has flanges at the end.

According to the present invention, a multipart chromatography column connection comprises a two-part screwed union anchored on the bead of a column body or on the thread of a metal column or a jacket surrounding the latter. The connection has an upper part and a lower part, a bushing, fixed therein, with a capillary and a sealing insert of soft plastic at the end. The upper part of the screwed union has a window in which a nut is arranged for free turning. The bushing has an external thread which meshes with the nut. The nut and bushing are made of a hard material. An adaptor, also made of hard material, is screwed to the lower end of the bushing, the capillary being held in sealing compression between the two parts. The sealing insert is screwed to the free end of the adaptor. The adaptor and sealing insert have mutually aligned bores, which are connected to the capillary, and have sealing surfaces bearing against one another.

Using a chromatography column of this structure, the compaction of the bed is possible directly and without additional aids and the bed no longer needs to be let down after the compaction.

The connection consists of different parts depending on the column body, and the bushing, the adaptor and the sealing insert can be constructed in the same way.

A first embodiment of the invention comprises a screwed union for a column body with connecting flanges at the end having an upper part with an external thread and a lower part with an internal thread and insertion ring. A second embodiment of the invention comprises a screwed union for a column body with an external thread at the end, having a fixing device with an internal thread, which can be screwed directly upon the column body. A third embodiment of the invention comprises a screwed union for a column body without connecting flanges at the end and without external threads, having a fixing device with an internal thread, which can be screwed directly upon a guard jacket surrounding the column body.

All the embodiments have, as common components, the bushing which serves as a guide for the capillary connection tube, the adaptor which holds the capillary tube with a clamping ring, and the sealing insert with frit. The column bodies can be made of glass, ceramic, sapphire glass or stainless steel.

The bushing has a through-bore for the capillary, the latter being held in compression between two hard materials (the bushing and the adaptor) by means of a clamping ring. Alternatively, the capillary can be flanged in the manner of a disk and held by a metal ring which stabilizes the flange. Both arrangements achieve high tightness of the connection between the capillary end and the sealing insert.

At the same time, a particularly simple structure results, since the bores in the adaptor and in the sealing insert, which correspond to the continuation of the capillary, can be kept very short and are easily produced. Material by the meter can be used for fabricating the bushing, because no special dimensional requirements have to be met by the internal bore which is to take the capillary.

According to the invention, the bushing is preferably made of an easily worked hard plastic or metal, and especially of metal such as aluminum or stainless steel. When metal is used, all fluid-bearing parts are kept free of contact with metallic surfaces.

A sealing insert of polytetrafluoroethylene (PTFE) has proved particularly suitable for the present invention, the combination with the sealing surfaces of the hard plastic adaptor in this case providing an increase in compressive strength, since the soft PTFE of the sealing insert is able to flow against irregularities in the adaptor.

As a result of the combination of the above-mentioned parts with a single or multiple lip seal on the sealing insert, high tightness is ensured and a low frictional resistance towards the inner surface of the column is obtained, so that the forces arising when the sealing insert is lowered against the column packing do not become unduly large.

Preferably, the adaptor is made of polychlorotrifluoroethylene (PCTFE) or polyetherether-ketone (PEEK), because the properties of these materials are particularly well matched for the present purpose to the PTFE of the sealing insert. Titanium has also proved to be very suitable as the material for the adaptor.

The capillary is preferably made of PEEK and, as stated above, is held between the bushing and adaptor by a clamping ring. It is also possible, however, to mold a disk-shaped rim (flange) to the end of the capillary and to place a metal washer on the tube side, the bushing resting on this washer. The disk-shaped flange is held in compression between the metal washer and the adaptor.

The present invention also relates to a method for filling a chromatography column. According to this method, the column is filled with a suspension of the packing material and compressed by means of a ram, carrier fluid emerging. According to the invention, the sealing insert is placed on top of the suspension and moved against the suspension by means of the bushing acting as a spindle. After compression of the suspension, during which a certain quantity of carrier fluid emerges, the column can immediately be used for the chromatographic separation of substances. The homogeneity of the column packing is no longer disturbed. Moreover, the height of the column bed can easily be readjusted during operation. The homogeneous structure of the column bed is thus retained, because the sealing insert ensures uniform repositioning of the column packing over the entire column cross-section.

FIG. 1 shows a multipart chromatography column connection for a chromatography column with glass body 15. The column glass body has flanges 16 at the end, on which the screwed union, which comprises an upper part with external thread 1 and a lower part with internal thread 2, is held by means of split insertion ring 17. In window 6 knurled nut 7 is arranged for free turning. For the same effect, the window can, for example, also be formed as a slot guide, in which case the knurled nut can be inserted from the side. Knurled nut 7 has an internal thread which interacts with the external thread of bushing 3 so that, when knurled nut 7 is turned, bushing 3 is raised or lowered. Bushing 3 penetrates, freely rotatably, upper part 1 and lower part 2 and protrudes into column body 15.

Adaptor 8 which, in this case, has a blind hole with internal thread, is screwed upon the lower part of bushing 3. Bushing 3 contains a through-bore into which capillary tube 4 is introduced. The latter carries at its lower end clamping ring 11 which engages in a conical recess of adaptor 8 and firmly surrounds the end of the capillary. As a result of bushing 3 being screwed to adaptor 8, clamping ring 11 is forced against the adaptor and surrounds capillary 4 making a seal. Bushing 3 and adaptor 8 are made of a hard material such as, for example, PCTFE. Preferably, however, the bushing is made of metal and the adaptor is made of PCTFE or PEEK.

Clamping ring 11 is aligned coaxially to bore 9 in adaptor 8. The adaptor engages with an abutting (or conical) sealing surface 12 into a blind hole of sealing insert 5. The latter is made of PTFE and carries an internal thread into which sealing insert 5 is screwed. Sealing insert 5 also has a through-bore which is aligned with capillary 4 and bore 9 in the adaptor and which is continued up to frit holder 18. For sealing against the inner surface of the column body, the sealing insert has a seal, preferably a triple seal, with lips 10. On the underside facing the column packing, the sealing insert has recess 18 which takes up the frit.

The two upper parts, bushing 3 and adaptor 8, are rigidly joined together by screwed union 26. Since they also are made of hard material, they are capable of transmitting shear forces to the sealing insert even over a considerable length. Because the sealing insert consists of soft material (PTFE), it is capable, even when deflections of adaptor 8 occur, of compensating for this movement without loss of tightness, under the action of the shear stress arising on compression.

Figure 2:
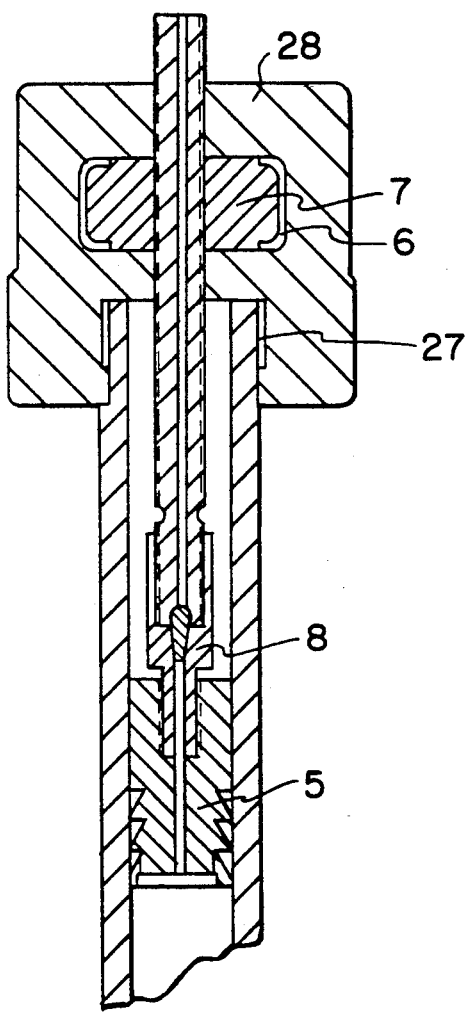
FIG. 2 show a second embodiment of a chromatography column connection according to the invention, in which the column body has external threads at the end.

FIG. 2 shows a multipart chromatography column connection for a chromatography column with a column body which carries external threads at the end. Fixing device 28 is screwed directly to external threads 27.

As in the first embodiment of FIG. 1, fixing device 28 takes up bushing 3. It also has window 6 in which knurled nut 7 is mounted for free turning. To the same effect the window can, for example, also be constructed in a slot design, in which case the knurled nut can be inserted from the side. Knurled nut 7 has an internal thread which interacts with the external thread of bushing 3 so that, when knurled nut 7 is turned, bushing 3 is raised or lowered. The construction of the bushing end of adaptor 8 screwed to bushing 3 with sealing insert 5 screwed thereto corresponds to the first embodiment of FIG. 1 in structure and function.

As a result of the direct screwing, a rigid structure is again obtained so that, as in the case of the first embodiment, during filling of the column the compressive forces required for expulsion can be transmitted via the busing and the adaptor to the sealing insert which bears against the suspension of the packing material slurry.

Figure 3:
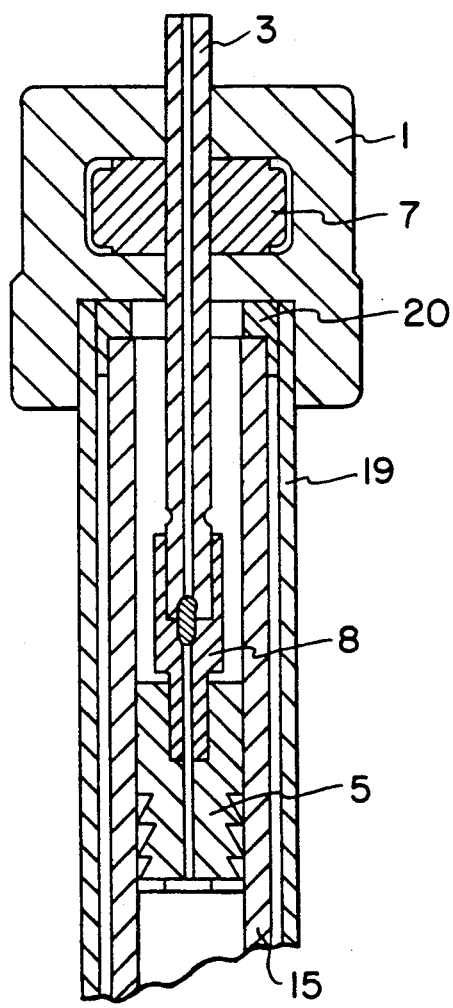
FIG. 3 shows a third embodiment of a chromatography column connection according to the invention, in which the column body has no flanges or external threads at the end, but which has a guard jacket.

FIG. 3 shows the third embodiment of the chromatography column connection, having column body 15 which has no flanges or external threads at the end. The column body is surrounded by guard jacket 19 which has an inspection window, so that the column body can be checked at any time. The guard jacket carries external threads 29 at the end, to one end of which upper part 1 is screwed. To ensure stable, centered seating of the glass body, crown 20 is placed on top of this end piece of the column body. Bushing 3, in the center of which the capillary runs, passes through the center of the crown. The construction of the bushing and of adaptor 8 screwed to bushing 3 with sealing insert 5 in turn screwed thereto corresponds to the first embodiment of FIG. 1 in structure and function.

As a result of the direct screwing, a rigid structure is again obtained so that, as in the case of the first embodiment of FIG. 1, during filling of the column the compression forces required for expulsion can be transmitted via the busing and the adaptor to the sealing insert which bears against the suspension of the packing material slurry.

Figure 4:
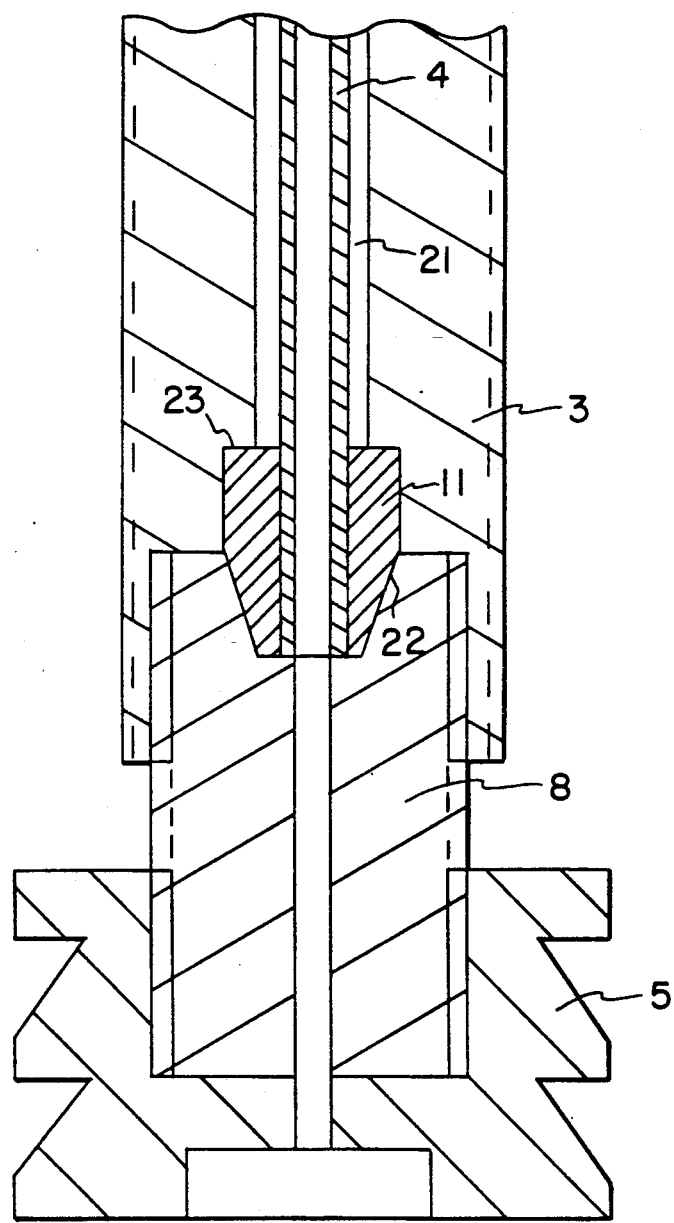
FIG. 4 shows an enlarged representation of the assembly of the bushing, adaptor and sealing insert located in the column interior.

FIG. 4 shows an enlarged representation of the assembly of bushing 3, adaptor 8 and sealing insert 5 located in the column interior. In bushing 3, there is through-bore 21 in which capillary 4 (of PEEK or metal) runs. This ends in clamping ring 11. Clamping ring 11 comprises lower cone 22 and rests in a counter-cone of adaptor 8. Bushing 3 has shoulder 23 which rests on clamping ring and which forces clamping ring 11 into the counter-cone when bushing 3 is screwed to adaptor 8 so that the elastic clamping ring firmly surrounds and seals the capillary. This clamping ring can also be designed in a known manner as a double cone or it can be provided with a cutting edge. Analogously, clamping ring 11 can of course also have an upper cone, in which case the counter-cone then has to be arranged in bushing 3.

Figure 5:
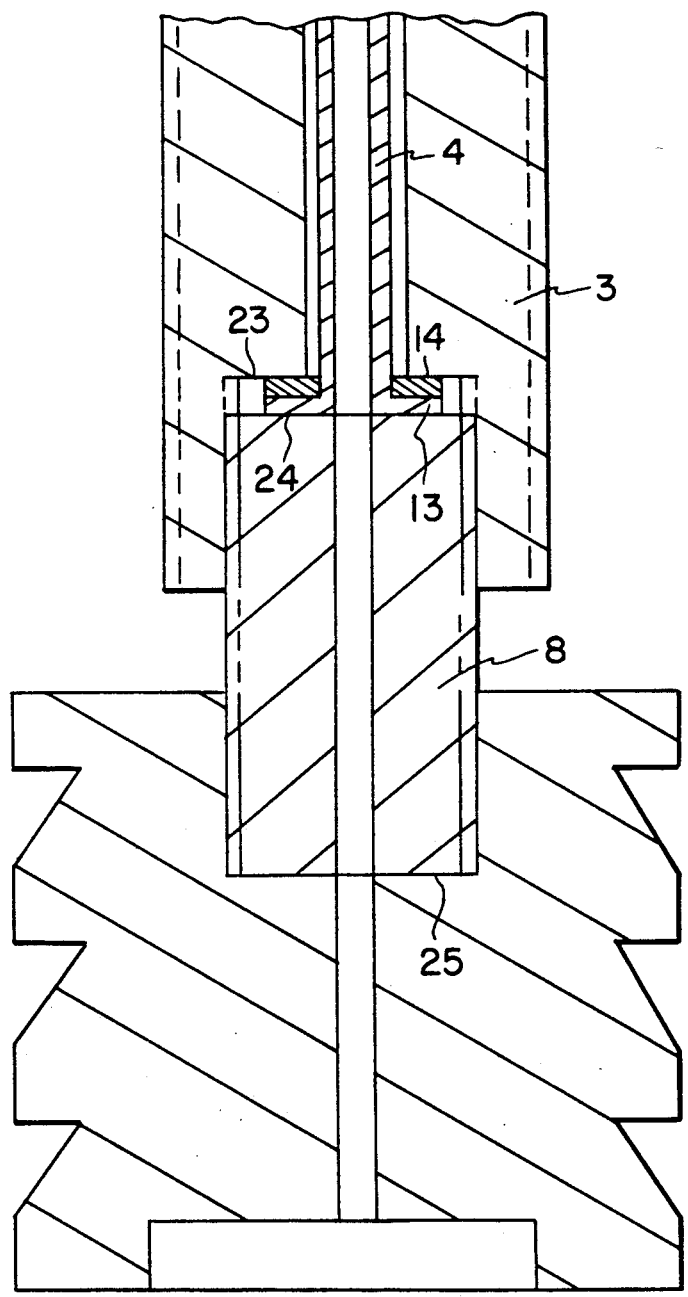
FIG. 5 shows the sealing of the capillary in the bushing by means of a washer.

FIG. 5 shows the variation in which capillary 4 is sealed in bushing 3 by means of washer 14. Washer 14 is forced by shoulder 23 onto disk 13 molded to the capillary and compresses the disk between itself and the here flat support surface 24 of adaptor 8. Adaptor 8 ends in a blind hole of sealing insert 5 and bears against bottom 25 thereof, in an abutting or conical manner.

The threads can be right-handed or left-handed threads, and the screwed union between bushing 3 and adaptor 8 can be made in the interior of adaptor 8 as shown in FIGS. 1, 2 and 3 or else in the interior of bushing 3 (FIGS. 4 and 5).

List of Reference Numerals

1. Upper Part
2. Lower Part
3. Bushing
4. Capillary Tube
5. Sealing Insert
6. Window
7. Knurled Nut
8. Adaptor
9. Bore
10. Lips
11. Clamping Ring
12. Sealing Surface
13. Disk
14. Washer
15. Column Glass Body
16. Flange
17. Insertion Ring
18. Frit Holder
19. Guard Jacket
20. Crown
21. Through-bore
22. Lower Cone
23. Shoulder
24. Support Surface
25. Bottom
26. Screwed Union
27. External Thread
28. Fixing Device
29. External Thread

What is claimed is:

1. A multipart chromatography column connection having a two-part screwed union anchored on a bead of a column body or on a thread of a metal column or its surrounding jacket, comprising
   an upper part having a window in which a nut is arranged for free turning;
   a bushing having an external thread which meshes with the nut;
   an adaptor screwed to a lower end of the bushing;
   a capillary held in sealing compression between the adaptor and the bushing; and
   a sealing insert screwed to the free end of the adaptor, wherein the adaptor and sealing insert have mutually-aligned bores which are connected to the capillary and which have sealing surfaces bearing against one another.

2. A chromatography column connection according to claim I, wherein the bushing and the nut are made of a hard material.

3. A chromatography column connection according to claim 2, wherein the adaptor is made of a hard material.

4. A chromatography column connection according to claim 3, wherein the bushing and the nut are made of a material selected from the group consisting of hard plastic and metal.

5. A chromatography column connection according to claim 4, wherein the bushing and the nut are made of a material selected from the group consisting of aluminum and steel.

6. A chromatography column connection according to claim 3, wherein the sealing insert is provided with a lip seal.

7. A chromatography column connection according to claim 3, wherein the adaptor is made of hard plastic.

8. A chromatography column connection according to claim 3, wherein the adaptor is made of a material selected from the group consisting of polychlorotrifluoroethylene and titanium.

9. A chromatography column connection according to claim 3, wherein the capillary is held between the bushing and adaptor by a clamping ring.

10. A chromatography column connection according to claim 3, wherein the capillary is held between the bushing and adaptor by a disk molded to the end of the capillary with a washer.

* * * * *